Figure 1:
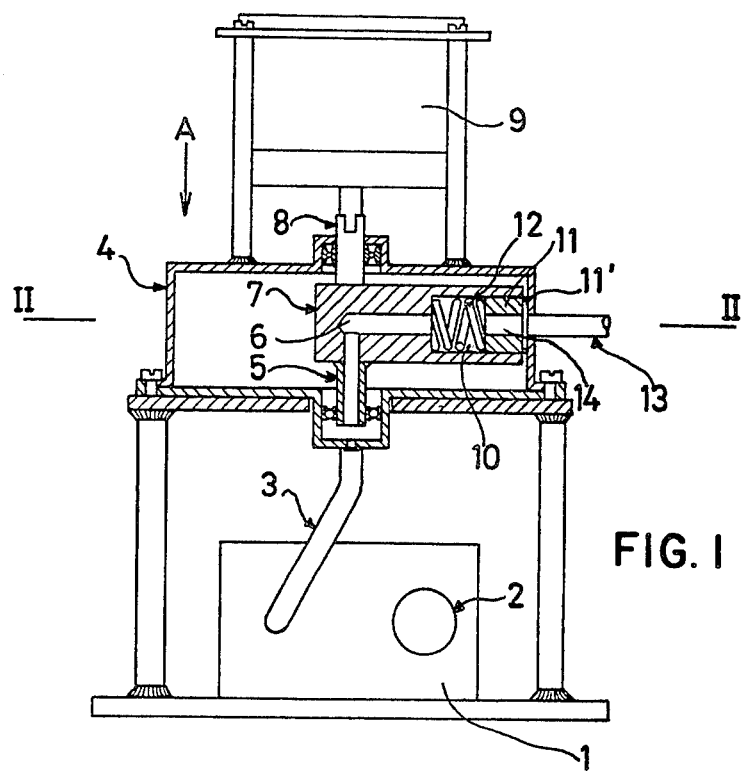

United States Patent [19]
Muller et al.

[11] 3,995,494
[45] Dec. 7, 1976

[54] DEVICE FOR THE TAKING OF AIR PROBES IN A SEQUENTIAL MANNER

[75] Inventors: Karl H. Muller, Casciago; Andre E. Sieffert, Cardana, both of Italy

[73] Assignee: European Atomic Energy Community (Euratom), Luxembourg

[22] Filed: Nov. 28, 1975

[21] Appl. No.: 635,948

[30] Foreign Application Priority Data
Nov. 27, 1974 Luxembourg .......................... 71369

[52] U.S. Cl. ..................... 73/421.5 R; 137/625.11; 141/114; 141/313
[51] Int. Cl.² ......................................... G01N 1/24
[58] Field of Search .......... 73/421.5 R, 424; 141/4, 141/10, 17, 114, 313; 137/625.11

[56] References Cited
UNITED STATES PATENTS

| | | |
|---|---|---|
| 2,333,934 | 11/1943 | Jacobson ...................... 73/421.5 R |
| 2,489,394 | 11/1949 | Austin ........................... 73/421.5 R |
| 3,034,528 | 5/1962 | Warff ............................ 137/625.11 |
| 3,186,434 | 6/1965 | Hrdina .......................... 137/625.11 |
| 3,921,456 | 11/1975 | Newcomb et al. ............. 73/421.5 R |

Primary Examiner—S. Clement Swisher
Attorney, Agent, or Firm—Stevens, Davis, Miller & Mosher

[57] ABSTRACT

An automatic sampling device for atmospheric probes to check the propagation of noxious airborne substances. A pump feeds a distributor having a bore therethrough which is pivotably mounted in a circular housing having a plurality of necks extending radially outwardly for the attachment of plastic bags to catch samples of air delivered thereto by the distributor.

7 Claims, 5 Drawing Figures

DEVICE FOR THE TAKING OF AIR PROBES IN A SEQUENTIAL MANNER

The invention concerns an automatic sampling device for atmospheric probes which is suitable in particular for determining the ventilation of a town and the propagation meteorology of noxious airborne substances.

Sampling devices have already been developed specifically for the determination of the atmospheric distribution of noxious substances. U.S. Pat. No. 2,699,679 concerns an apparatus for determining the precipitation of noxious substances as a function of wind direction and wind velocity. In this known device, a distributor mechanism is accordingly actuated by the wind.

The purpose of the invention, however, is in the first place to determine the time dependence of the pollution and indirectly to measure other special factors such as wind direction, climatic influences, etc., by the evaluation of a number of probes from devices which are distributed throughout the entire test area.

A correlation analysis then permits, from the space-time measurement data of the concentrations of noxious substances or indicators, the derivation of transfer functions whose structure and characteristic parameters take account of the meteorological and topographical features of an urban area and its immediate vicinity, for example.

Sampling devices of this kind must comply with certain requirements. They must work as automatically as possible and be simple to use, weatherproof, robust and of low cost. The last requirement follows from the need to provide every town with its own sampling system so that the decisions which have to be taken time and again in questions concerning the location of future emitters can be given an independent experimental basis.

Furthermore, sampling devices of this kind must be constructed in such a manner that the program of the samples taken can be varied within wide limits and adapted to all the circumstances arising.

The aim of the invention is to create an automatic sampling device of this kind. In accordance with the invention, this aim is achieved by arranging that each sampling device has a distributor with a bore passing through it, the distributor being pivotably mounted, in a distributor housing having apertures, on a hollow spindle in such a manner that the mouth of the bore during rotation passes across at least one of the apertures mentioned whereby the hollow spindle is connected on the one side to the bore and on the other to the pressure side of an air pump drawing in air from its surroundings and the distributor is driven by a shaft whose rotation controls the beginning, sequence and duration of the probes taken as a function of the local distribution of apertures on the distributor housing.

The shaft is preferably driven via a mechanical clock.

During the working process, the mechanical clock turns the distributor arm past the said apertures which are advantageously arranged as necks for plastic bags. Meanwhile the air pump forces the incoming air through the hollow spindle of the distributor and the bore of the distributor arm and via the necks into the plastic bag attached to each of them, the bags having first been evacuated. A commercially available plastic bag can advantageously be used for this, consisting of two superimposed plastic sheets of identical dimensions welded together at three of the four edges. The fourth edge is welded together after the insertion of a connection piece, for example of plastic. The two plastic sheets then fully adhere to each other until they are separated by the air pumped into the bag. The electrical power requirement for the pump can be supplied by dry batteries.

The said components are preferably mounted in a weatherproof box which can be advantageously attached to a wire frame such as is often used in households. The plastic bags can then be arranged in the interior of the basket and thus adequately supported.

Before the beginning of every experiment, the sampling devices are taken with a transport means to the measurement locations in question. The clocks are set there to the pre-determined running times, after the expiry of which the pumps then transfer the air samples to the sacks. After the conclusion of the experiment, the sampling devices are collected again and the contents of the bags subjected to analysis by gas-chromatography for example in the laboratory.

The invention is explained in the following with the aid of schematic drawings of examples of execution with further details.

Figure 2:
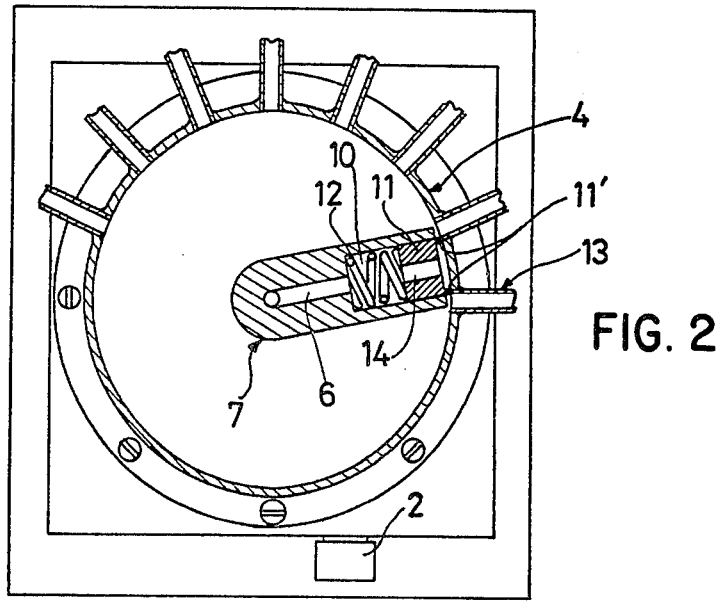
Figure 3:
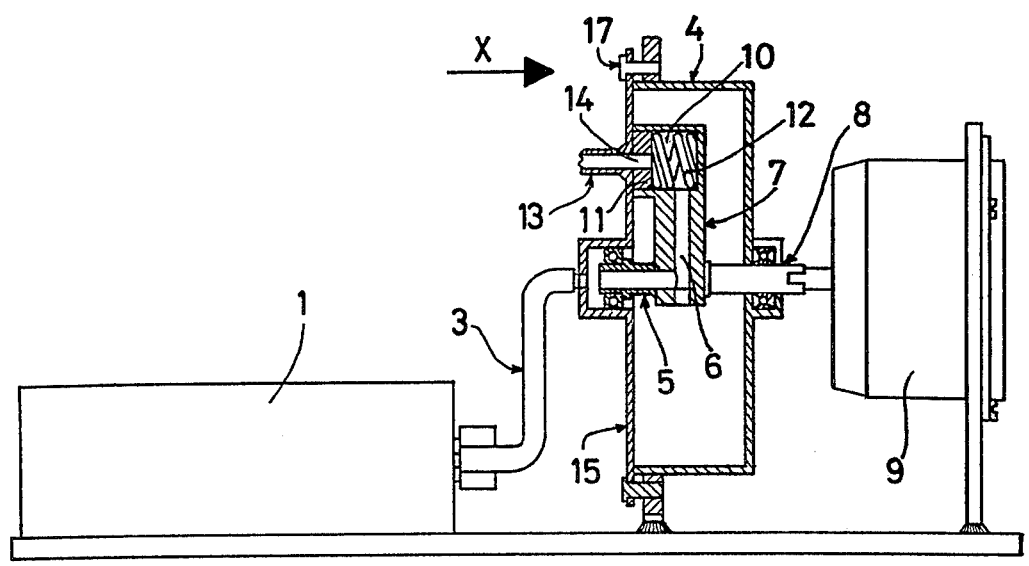
Figure 4:
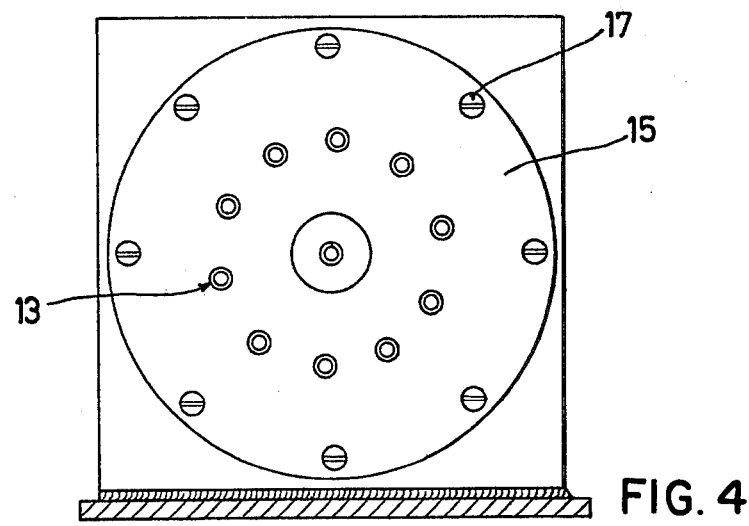
Figure 5:
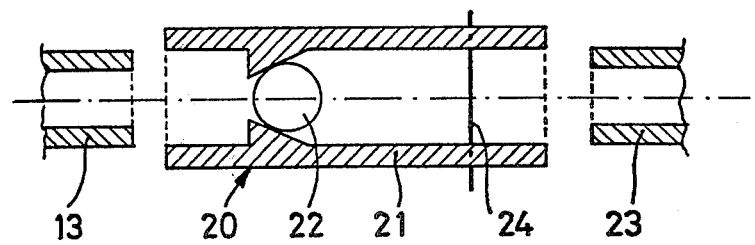

There is shown in:

FIG. 1 a view of the clockwork mechanism, distributor and pump with a section through the distributor and distributor housing;

FIG. 2 a view looking towards A of FIG. 1 in section along line II—II of FIG. 1;

FIG. 3 a view of a second embodiment of the sampling device in accordance with the invention, likewise with a section through the distributor;

FIG. 4 a view looking towards X of FIG. 3 of the front of the distributor;

FIG. 5 a lengthwise section through a simple check valve which is arranged between the connection piece of the plastic bag and the neck of the distributor housing.

The device shown in FIG. 1 comprises a diaphragm pump 1 of approximately 1.5 liters/minute dumping capacity with intake aperture 2 and connection hose 3 through which the incoming air is pumped to the distributor housing 4 from where it is passed via the pivotably mounted hollow spindle 5 to the bore 6 of the distributor arm 7. The distributor arm 7 is driven in a rotary movement by a mechanical clock 9 via the shaft 8. At the end part of the distributor arm 7 the bore 6 changes to an enlarged cylindrical bore 10, presenting a sliding surface for a plunger piston 11 with a central bore 14. The piston 11 is lightly pressed against the cylindrical jacket of the distributor housing by the helical spring 12. The piston is preferably provided with a cylindrical lip 11' which aids the guidance of the current of air and causes only slight friction with the distributor jacket. As can be seen from FIG. 2, the air passed by the diaphragm pump can escape via a neck 13 into the plastic bag (not shown), which has been evacuated before being attached to the latter, when the distributor arm is in a suitable position.

The device described has an advance movement. In this, the distributor arm passes across the part of the distributor jacket not provided with necks; the incoming air escapes unused to atmosphere, e.g., through a slot (not shown) in the part of the distributor jacket not provided with necks or through necks not fitted with bags. Whereas in the embodiment described the necks are arranged on the distributor jacket whereby the sampling program is largely fixed as a function of the running cycle of the clockwork mechanism, the second embodiment described below and as shown in FIGS. 3 and 4 is provided with an interchangeable front panel 15 having holes 16 and fitted with necks, being fixed by easily detachable screw connections 17 to the distributor housing. In these illustrations, constructional elements are marked with the same numbers as elements with a similar function in FIG. 1. As can be seen from FIG. 4, which represents a view of the front panel 15 looking in direction X as shown in FIG. 3, the sampling program is adjusted to the circumstances in question by interchanging front panels with a different hole congifuration.

FIG. 5 shows a lengthwise section, aligned with the neck 13 of the distributor housing and the connection piece of a plastic bag (not shown, of a cylindrical check valve 20 with a valve cylinder 21, a rubber ball 22 and a piece of wire 24 for retaining the ball. To establish a connection, the check valve is pushed on to the neck 13 and the plastic connection piece 23 is inserted in the valve cylinder 21. The pressure of the current of air emerging at the neck is sufficient to open the valve.

For those skilled in the art, it is clear that the variations of the invention described can be modified and adapted in many respects.

Thus it is possible to arrange various circles of holes on the front panel whereby a simple mechanism permits the transition from one circle of holes to another. The advance movement and the interval between the samples taken can also be varied within wide limits by interposing a reduction element between the clock and the distributor.

We claim:

1. Automatic sampling device for atmospheric probes which enables a sampling program to be varied within wide limits, comprising a distributor having a full-length bore and pivotably mounted in a distributor housing having apertures on a hollow spindle in such a manner that the mouth of the bore during rotation passes across at least one of said apertures whereby the hollow spindle is connected on the one side to the bore and on the other to the pressure side of an air pump drawing in air from its surroundings and the distributor is driven by a shaft whose rotation controls the beginning, sequence and duration of the probes taken as a function of the local distribution of apertures on the distributor housing.

2. Device as recited in claim 1, wherein the apertures are arranged as necks for plastic bags.

3. Device as recited in claim 2, wherein the necks are each connected to the plastic bags via a cylindrical check valve.

4. Device as recited in claim 1, wherein the apertures are arranged on the jacket surface of a cylindrical distributor housing.

5. Device as recited in claim 1, wherein the apertures are arranged on an interchangeable front panel of the distributor housing.

6. Device as recited in claim 1, wherein the distributor is driven via the shaft of a mechanical timer.

7. Device as recited in claim 5, wherein the apertures on the front panel form at least one circle.

* * * * *